(12) United States Patent
Eilert et al.

(10) Patent No.: US 12,165,696 B2
(45) Date of Patent: Dec. 10, 2024

(54) SIGNAL ROUTING BETWEEN MEMORY DIE AND LOGIC DIE

(71) Applicant: Micron Technology, Inc., Boise, ID (US)

(72) Inventors: Sean S. Eilert, Penryn, CA (US); Glen E. Hush, Boise, ID (US); Aliasger T. Zaidy, Seattle, WA (US); Kunal R. Parekh, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 197 days.

(21) Appl. No.: 17/830,981

(22) Filed: Jun. 2, 2022

(65) Prior Publication Data

US 2023/0046050 A1 Feb. 16, 2023

Related U.S. Application Data

(60) Provisional application No. 63/231,660, filed on Aug. 10, 2021.

(51) Int. Cl.
*G11C 7/10* (2006.01)
*G06F 3/06* (2006.01)
(Continued)

(52) U.S. Cl.
CPC ........ *G11C 11/4093* (2013.01); *G06F 3/0656* (2013.01); *G06F 13/1673* (2013.01); *G06F 13/28* (2013.01); *G11C 7/08* (2013.01); *G11C 7/1039* (2013.01); *G11C 11/4087* (2013.01); *G11C 11/4091* (2013.01); *G11C 11/4096* (2013.01); *G16B 30/00* (2019.02); *G16B 50/10* (2019.02); *H01L 21/78* (2013.01); *H01L 22/12* (2013.01); *H01L 24/08* (2013.01); *H01L 24/48* (2013.01); *H01L 24/80* (2013.01); *H01L 25/0652* (2013.01); *H01L 25/0657* (2013.01); *H01L 25/18* (2013.01); *H01L 25/50* (2013.01); *G06F 2213/28* (2013.01); *H01L 24/16* (2013.01); *H01L 2224/0801* (2013.01); *H01L 2224/08145* (2013.01); *H01L 2224/1601* (2013.01); *H01L 2224/16221* (2013.01); *H01L 2224/48091* (2013.01); *H01L 2224/48145* (2013.01); *H01L 2224/48221* (2013.01); *H01L 2224/80895* (2013.01);
(Continued)

(58) Field of Classification Search
CPC ..... G11C 11/4093; G11C 7/08; G11C 7/1039; G11C 11/4087; G11C 11/4091; G11C 11/4096; G16B 50/10; G16B 30/00; G06F 3/0656; G06F 13/1673; G06F 13/28; H01L 21/78; H01L 22/12
USPC ...................................... 365/189.05
See application file for complete search history.

(56) References Cited

U.S. PATENT DOCUMENTS 9,344,091 B2 5/2016 Jayasena et al.
9,577,644 B2 2/2017 Gao et al.
(Continued)

*Primary Examiner* — Viet Q Nguyen
(74) *Attorney, Agent, or Firm* — Brooks, Cameron & Huebsch, PLLC

(57) ABSTRACT

A memory device includes a memory die bonded to a logic die via a wafer-on-wafer bond. A controller of the memory device that is coupled to the memory die can activate a row of the memory die. Responsive to activating the row, a sense amplifier stripe of the memory die can latch a first plurality of signals. A transceiver can route a second plurality of signals from the sense amplifier stripe to the logic die.

17 Claims, 8 Drawing Sheets

(51) Int. Cl.
*G06F 13/16* (2006.01)
*G06F 13/28* (2006.01)
*G11C 7/08* (2006.01)
*G11C 11/408* (2006.01)
*G11C 11/4091* (2006.01)
*G11C 11/4093* (2006.01)
*G11C 11/4096* (2006.01)
*G16B 30/00* (2019.01)
*G16B 50/10* (2019.01)
*H01L 21/66* (2006.01)
*H01L 21/78* (2006.01)
*H01L 23/00* (2006.01)
*H01L 25/00* (2006.01)
*H01L 25/065* (2023.01)
*H01L 25/18* (2023.01)

(52) U.S. Cl.
CPC ............... *H01L 2224/80896* (2013.01); *H01L 2225/06517* (2013.01); *H01L 2225/06524* (2013.01); *H01L 2225/06527* (2013.01); *H01L 2225/06541* (2013.01); *H01L 2225/06565* (2013.01); *H01L 2225/06589* (2013.01); *H01L 2924/1431* (2013.01); *H01L 2924/14335* (2013.01); *H01L 2924/1436* (2013.01)

(56) References Cited

U.S. PATENT DOCUMENTS

| | | | |
|---|---|---|---|
| 9,972,611 B2 | 5/2018 | Pappu et al. | |
| 10,157,792 B2* | 12/2018 | Zhang | H01L 21/76828 |
| 10,256,055 B2* | 4/2019 | Amano | H01H 13/06 |
| 10,680,025 B2* | 6/2020 | Shim | H01L 27/1469 |
| 10,749,528 B2* | 8/2020 | Atsatt | G11C 15/00 |
| 10,756,055 B2* | 8/2020 | Kang | H01L 24/94 |
| 10,879,294 B2* | 12/2020 | Kim | H04N 25/75 |
| 11,430,766 B2 | 8/2022 | Liu et al. | |
| 11,456,300 B2* | 9/2022 | Lu | H01L 25/0657 |
| 11,594,469 B2* | 2/2023 | Ku | H01L 24/97 |
| 11,637,140 B2* | 4/2023 | Kim | H01L 27/14636 |
| | | | 250/208.1 |
| 11,877,439 B2* | 1/2024 | Lu | H01L 27/0688 |
| 2003/0206430 A1* | 11/2003 | Ho | G11C 11/22 |
| | | | 365/145 |
| 2017/0263306 A1 | 9/2017 | Murphy et al. | |
| 2019/0012116 A1* | 1/2019 | Gutala | G06F 3/0632 |
| 2020/0243486 A1 | 7/2020 | Quader et al. | |
| 2022/0223494 A1* | 7/2022 | Lee | F28D 15/04 |

* cited by examiner

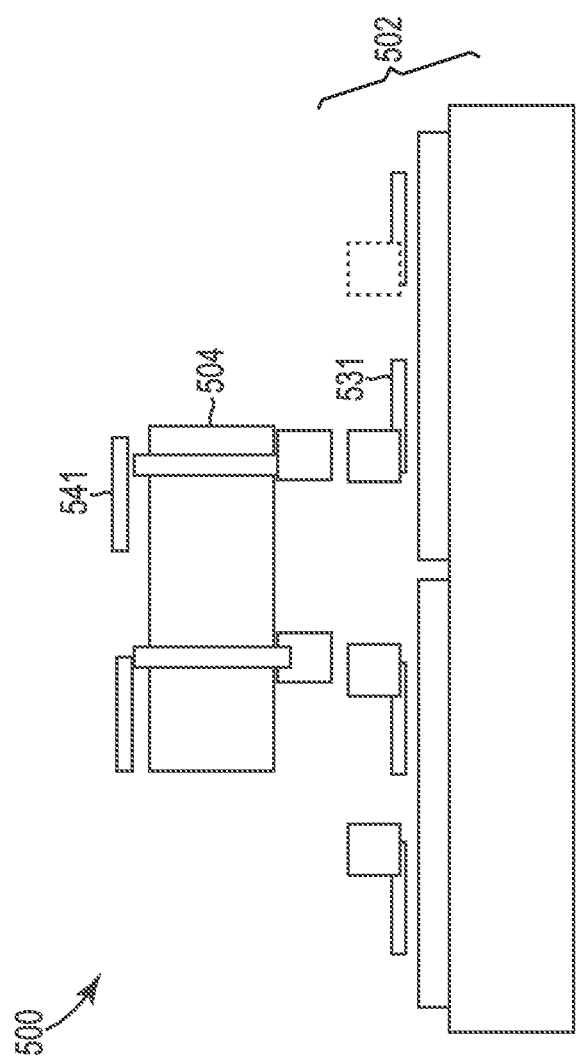

SIGNAL ROUTING BETWEEN MEMORY DIE AND LOGIC DIE

PRIORITY INFORMATION

This application is a non-provisional application of U.S. application Ser. No. 63/231,660, filed Aug. 10, 2021, the contents of which are included herein by reference.

TECHNICAL FIELD

The present disclosure relates generally to memory, and more particularly to apparatuses and methods associated with a memory device for routing signals between a memory die and a logic die.

BACKGROUND

Memory devices are typically provided as internal, semiconductor, integrated circuits in computers or other electronic devices. There are many different types of memory including volatile and non-volatile memory. Volatile memory can require power to maintain its data and includes random-access memory (RAM), dynamic random access memory (DRAM), and synchronous dynamic random access memory (SDRAM), among others. Non-volatile memory can provide persistent data by retaining stored data when not powered and can include NAND flash memory, NOR flash memory, read only memory (ROM), Electrically Erasable Programmable ROM (EEPROM), Erasable Programmable ROM (EPROM), and resistance variable memory such as phase change random access memory (PCRAM), resistive random access memory (RRAM), and magnetoresistive random access memory (MRAM), among others.

Memory is also utilized as volatile and non-volatile data storage for a wide range of electronic applications. including, but not limited to personal computers, portable memory sticks, digital cameras, cellular telephones, portable music players such as MP3 players, movie players, and other electronic devices. Memory cells can be arranged into arrays, with the arrays being used in memory devices.

BRIEF DESCRIPTION OF THE DRAWINGS

FIG. 5 illustrates a memory die and a logic die in accordance with a number of embodiments of the present disclosure.

DETAILED DESCRIPTION

Figure 1:
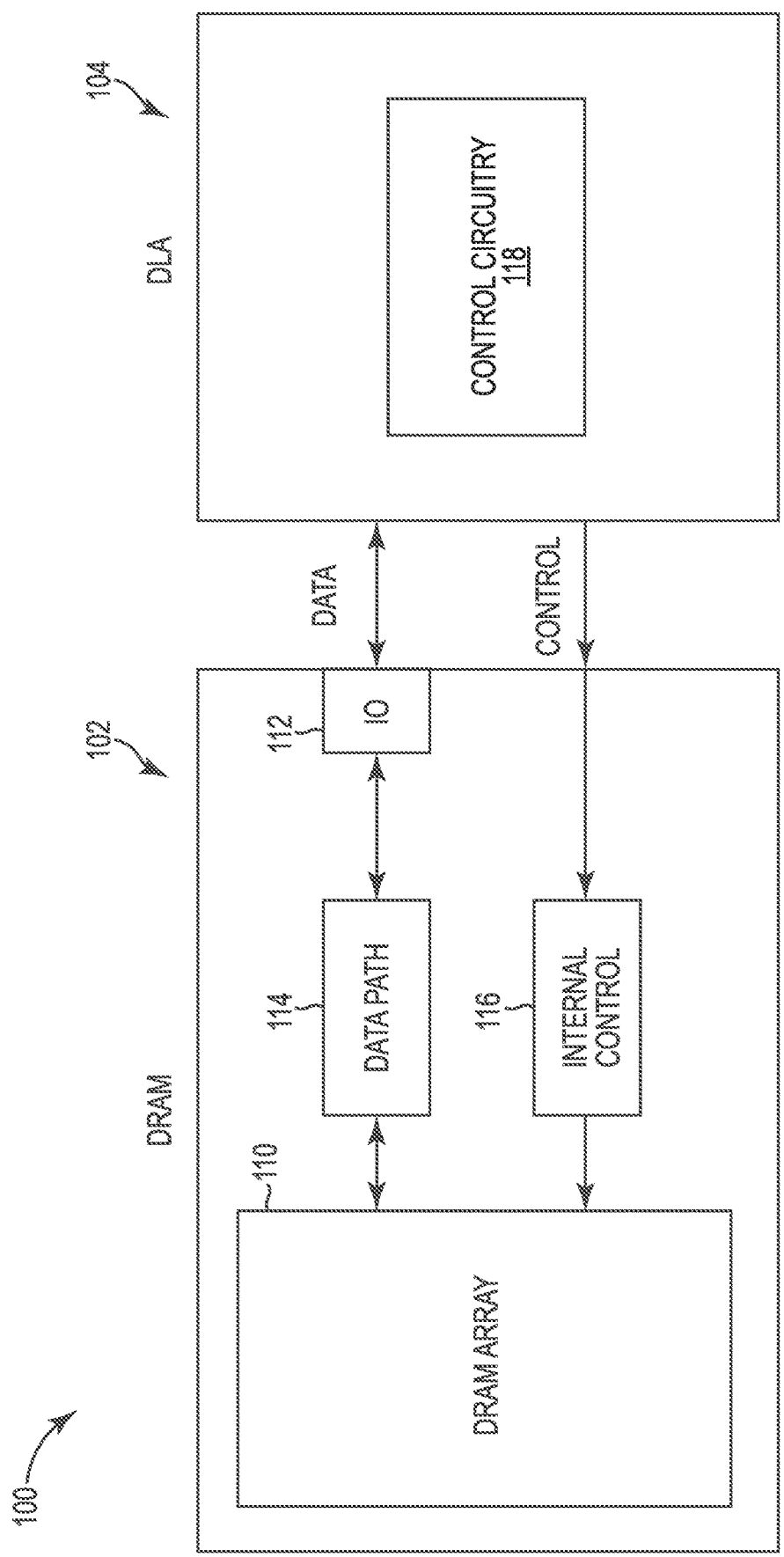
FIG. 1 illustrates a block diagram of an apparatus in the form of a system including a memory device and a logic device in accordance with a number of embodiments of the present disclosure.

The present disclosure includes apparatuses and methods related to a memory device for routing signals between memory die and logic die. Inexpensive and energy-efficient logic devices have been proposed. Such devices can benefit from being tightly coupled to memory devices. Logic devices can be accelerators. Accelerators can include artificial intelligence (AI) accelerators such as deep learning accelerators (DLAs).

AI refers to the ability to improve a machine through "learning" such as by storing patterns and/or examples which can be utilized to take actions at a later time. Deep learning refers to a device's ability to learn from data provided as examples. Deep learning can be a subset of AI. Neural networks, among other types of networks, can be classified as deep learning. The low power, inexpensive design of deep learning accelerators can be implemented in internet-of-things IOT devices. The DLAs can process and make intelligent decisions at run-time. Memory devices including the edge DLAs can also be deployed in remote locations without cloud or offloading capability.

A three-dimensional integrated circuit (3D IC) is a metal-oxide semiconductor (MOS) IC manufactured by stacking semiconductor wafers or dies and interconnecting them vertically using, for example, through-silicon vias (TSVs) or metal connections, to function as a single device to achieve performance improvements at reduced power and smaller footprint than conventional two-dimensional processes. Examples of 3D ICs include hybrid memory cube (HMC) and high bandwidth memory (HBM), among others.

Implementing a memory device that couples memory die and logic die using 3D IC can benefit from the efficient transfer of data between the memory die and the logic die. Transferring data from the memory die to the logic die can include transferring data from the memory die to a global data bus and transferring the data from the global data bus to the logic die. However, transferring data from the global data bus to the logic die can be inefficient.

Aspects of the present disclosure address the above and other deficiencies. For instance, at least one embodiment of the present disclosure can provide high bandwidth via a wide bus between a memory die and a logic die bonded via a wafer-on-wafer bonding process. The bus between the memory die and the logic die can be implemented such that data is transferred to the logic die without going through a global data bus. Transferring data, between the memory die and the logic die, using the wide bus can be more efficient than transferring data via the global data bus.

The figures herein follow a numbering convention in which the first digit or digits correspond to the drawing figure number and the remaining digits identify an element or component in the drawing. Similar elements or components between different figures may be identified by the use of similar digits. For example, 100 references element "00" in FIG. 1, and a similar element is referenced as 200 in FIG. 2. Analogous elements within a Figure may be referenced with a hyphen and extra numeral or letter. See, for example, elements 663-1, 663-2 in FIG. 6. As will be appreciated, elements shown in the various embodiments herein can be added, exchanged, and/or eliminated so as to provide a number of additional embodiments of the present disclosure.

In addition, as will be appreciated, the proportion and the relative scale of the elements provided in the figures are intended to illustrate certain embodiments of the present invention and should not be taken in a limiting sense.

FIG. 1 illustrates a block diagram of an apparatus in the form of a system 100 including a memory device 102 and a logic device 104 in accordance with a number of embodiments of the present disclosure. As used herein, a memory device 102, memory array 110, and/or a logic device 104, for example, might also be separately considered an "apparatus."

In this example, the system 100 includes a memory device 102 coupled to the logic device 104 via an interface 112 (e.g., an input/output "IO" interface). The system 100 can be part of a personal laptop computer, a desktop computer, a digital camera, a mobile telephone, a memory card reader, a server, or an Internet-of-Things (IoT) enabled device among various other types of systems. The system 100 can include separate integrated circuits, or both the memory device 102 and the logic device 104 can be on the same integrated circuit. The logic device 104 can be an artificial intelligence (AI) accelerator, which is also referred to herein as a deep learning accelerator (DLA) as an example. The logic device 104 can be referred to herein as a DLA 104. The DLA 104 can be implemented on an edge of the system 100. For example, the DLA 104 can be implemented external to the memory device 102. The DLA 104 can be coupled to the IO circuitry 112 and thus to a data path 114, which is coupled to the memory array 110.

In various examples, the DLA 104 can be bonded to the memory device 102. For example, a memory die of the memory device can be bonded to a logic die of the DLA 104. The logic die 104 can include control circuitry 118. The control circuitry 118 can control transceivers of the logic die 104 to route data from the memory device 102 to the logic die 104 via a wafer-on-wafer bond that couple the memory die to the logic die.

For clarity, the system 100 has been simplified to focus on features with particular relevance to the present disclosure. The memory array 110 can be a DRAM array, SRAM array, STT RAM array, PCRAM array, TRAM array, RRAM array, NAND flash array, NOR flash array, and/or 3D cross-point array for instance. The memory array 110 is referred to herein as a DRAM array as an example. The array 110 can comprise memory cells arranged in rows coupled by access lines (which may be referred to herein as word lines or select lines) and columns coupled by sense lines (which may be referred to herein as digit lines or data lines). Although the memory array 110 is shown as a single memory array, the memory array 110 can represent a plurality of memory arrays arranged in banks of the memory device 102.

Although not specifically illustrated, the memory device 102 includes address circuitry to latch address signals provided over a host interface. The host interface can include, for example, a physical interface (e.g., a data bus, an address bus, and a command bus, or a combined data/address/command bus) employing a suitable protocol. Such protocol may be custom or proprietary, or the host interface may employ a standardized protocol, such as Peripheral Component Interconnect Express (PCIe), Gen-Z interconnect, cache coherent interconnect for accelerators (CCIX), or the like. Address signals are received and decoded by a row decoder and a column decoder to access the memory array 110. Data can be read from memory array 110 by sensing voltage and/or current changes on the sense lines using sensing circuitry. The sensing circuitry can be coupled to the memory array 110. Each memory array 110 and corresponding sensing circuitry can constitute a bank of the memory device 102. The sensing circuitry can comprise, for example, sense amplifiers that can read and latch a page (e.g., row) of data from the memory array 110. The IO circuitry 112 can be used for bi-directional data communication with the logic device 104 along a data path 114. Read/write circuitry is used to write data to the memory array 110 or read data from the memory array 110. The read/write circuitry can include various drivers, latch circuitry, etc.

The control circuitry 116 (e.g., internal control) can decode signals provided by the host. The signals can be commands provided by the host. These signals can include chip enable signals, write enable signals, and address latch signals that are used to control operations performed on the memory array 110, including data read operations, data write operations, and data erase operations. In various embodiments, the control circuitry 116 is responsible for executing instructions from the host. The control circuitry 116 can comprise a state machine, a sequencer, and/or some other type of control circuitry, which may be implemented in the form of hardware, firmware, or software, or any combination of the three. In some examples, the host can be a controller external to the memory device 102. For example, the host can be a memory controller which is coupled to a processing resource of a computing device. Data can be provided to the logic device 104 and/or from the logic device 104 via data lines coupling the logic device 104 to the IO circuitry 112.

The DLA 104 can also be coupled to the control circuitry 116. The control circuitry 116 can control the DLA 104. For example, the control circuitry 116 can provide signaling to the row decoder and the column decoder to cause the transferring of data from the memory array 102 to the DLA 104 to provide an input to the DLA 104 and/or an artificial neural network (ANN) which is hosted by the DLA 104. The control circuitry 116 can also cause the output of the DLA 104 and/or the ANN to be provided to the IO circuitry 112 and/or be stored back to the memory array 110.

The ANN model can be trained by the DLA 104, the control circuitry 116, and/or by the external host (not specifically illustrated). For example, the host and/or the control circuitry 116 can train an ANN model which can be provided to the DLA 104. The DLA 104 can implement the trained ANN model as directed by the control circuitry 116. The ANN can be trained to perform a desired function.

After fabrication of the electronic devices (e.g., memory device 102 and DLA 104) on a first wafer and a second wafer, the first wafer and the second wafer can be diced (e.g., by a rotating saw blade cutting along streets of the first wafer and the second wafer). However, according to at least one embodiment of the present disclosure, after fabrication of the devices on the first wafer and the second wafer, and prior to dicing, the first wafer and the second wafer can be bonded together by a wafer-on-wafer bonding process. Subsequent to the wafer-on-wafer bonding process, the dies (e.g., memory die and logic die) can be singulated. For example, a memory wafer can be bonded to a logic wafer in a face-to-face orientation meaning that their respective substrates (wafers) are both distal to the bond while the memory dies and logic dies are proximal to the bond. This enables individual memory die and logic die to be singulated together as a single package after the memory wafer and the logic wafer are bonded together.

Figure 2:
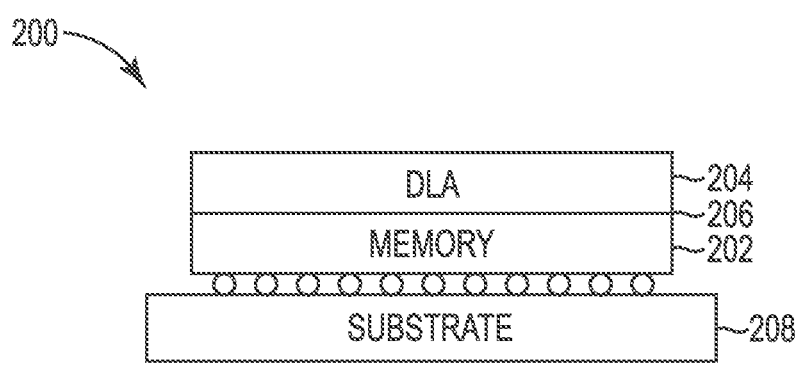
FIG. 2 illustrates a portion of bonded wafers including a memory die and a logic die in accordance with a number of embodiments of the present disclosure.

FIG. 2 illustrates a portion of the bonded wafers including a memory die 202 and a logic die 204 in accordance with a number of embodiments of the present disclosure. The memory die 202 is illustrated as being bonded to a substrate 208, however, in at least one embodiment, the logic die 204 can be bonded to the substrate 208 instead of the memory die 202. The substrate 208, memory die 202, bond 206, and logic die 204 can form a system 200, such as an integrated circuit, configured to perform one or more desired functions. Although not specifically illustrated, the substrate 208 can include additional circuitry to operate, control, and/or communicate with the memory die 202, logic die 204, and or other off-chip devices.

According to at least one embodiment of the present disclosure, the typical functionality of the memory die 202 does not change for typical memory operations. However, data can alternatively be transferred from the memory die 202 to the logic die 204 directly via the bond 206 instead of being routed through the typical input/output circuitry of the memory die 202. For example, a test mode and/or refresh cycle of the memory die 202 can be used to transfer data to and from the logic die 204 via the bond 206 (e.g., via LIOs of the memory die 202). Using the refresh cycle for an example existing DRAM memory device, with 8 rows per bank active and a refresh cycle time of 80 nanoseconds (versus 60 nanoseconds for a single row) with 4 banks in parallel and 16 nanosecond bank sequencing, the bandwidth would be 443 gigabytes/second. However, according to at least one embodiment of the present disclosure, with the wafer-on-wafer bond 206, with 32 rows per bank active, the refresh cycle time can approach 60 nanoseconds for 32 banks in parallel and without bank sequencing, the bandwidth is 5 terabytes/second using 8 watts. Such a significant bandwidth of data being sent from the memory device would overwhelm a typical interface and/or host device. However, certain logic devices (such as a DLA) can be configured to make use of that data bandwidth via the connections provided by the bond 206. Reduced off-chip movement of data can help reduce the power consumption associated with operating the memory in this fashion. Some embodiments of the present disclosure can provide, for example, a 70× performance increase in depthwise separable networks and/ or a 130× performance increase on natural language processing (NLP)/recommendation systems as compared to some current solutions. When implemented in an edge server, for example, some embodiments of the present disclosure can provide 16-32× memory bandwidth versus current solutions.

Although not specifically illustrated, multiple memory die 202 can be stacked on one another via a bond analogous to the bond 206. Alternatively, or additionally, TSVs can be used for communication of data between or through stacked memory die 202. The bond pads between stacked memory die 202 can be at locations that are replicated on stacked memory die 202 in a vertical orientation (as illustrated) such that the stacked memory die 202 are in alignment. The stacked memory die 202 can be formed by a conventional process or by wafer-on-wafer bonding (between different memory wafers) in different embodiments.

Although not specifically illustrated, the die that is bonded to the substrate 208 (e.g., the memory die 202 (as illustrated) or the logic die 204) can have TSVs formed therein to enable communication with circuitry external to the memory die 202 and logic die 204. The TSVs can also be used to provide power and ground contacts. Compared to the contacts provided by wafer-on-wafer bonding, TSVs generally have greater capacitance and a larger pitch and do not have as great of a bandwidth.

Although not specifically illustrated, in some embodiments an additional component can be bonded to the system 200. For example, a thermal solution component can be bonded to the top of the logic die 204 to provide cooling for the system 200. The physically close connection between the logic die 204 and the memory die 202 may generate heat. The thermal solution can help dissipate heat for the system 200.

Although not specifically illustrated, in some embodiments an additional component (non-volatile memory) can be bonded to the system 200 (e.g., in order to persistently store a model for the ANN). However, in some embodiments, the non-volatile memory is not necessary because the models may be relatively small and frequently updated.

Figure 3:
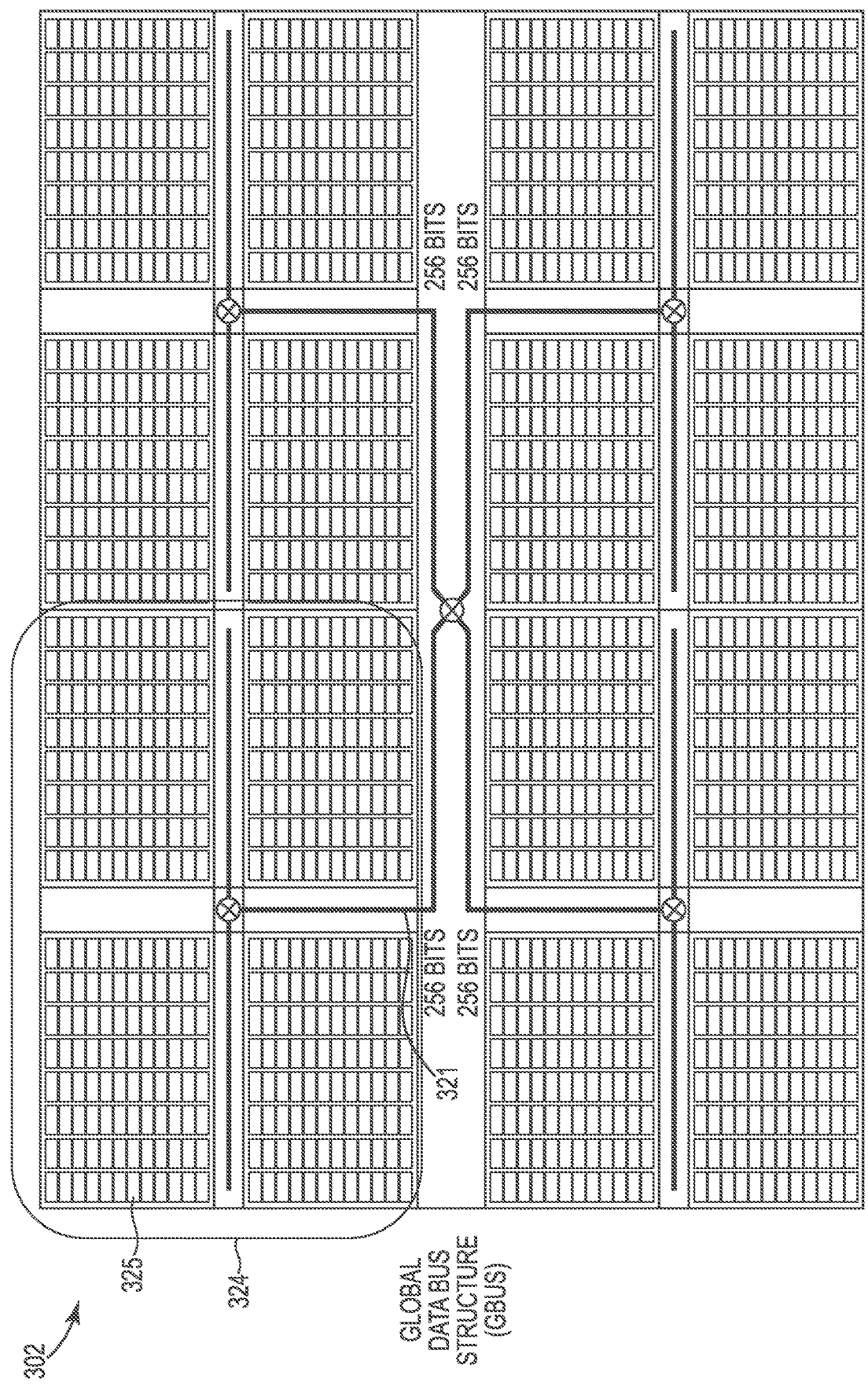
FIG. 3 illustrates a circuit diagram of a memory die in accordance with a number of embodiments of the present disclosure.

FIG. 3 illustrates a circuit diagram of a memory die 302 in accordance with a number of embodiments of the present disclosure. The example memory die 302 includes 16 memory banks 325 arranged in bank groups 324 of 4 banks. Each bank group 324 is coupled to a global data bus (GBUS) 321 (e.g., a 256 bit wide bus). Embodiments are not limited to these specific examples. The global data bus 321 can be modeled as a charging/discharging capacitor. The global data bus 321 can conform to a memory standard for sending data from the memory die 302 via an IO bus. However, although not specifically illustrated in FIG. 3, according to at least one embodiment of the present disclosure, a logic die coupled to the memory die 302 via a wafer-on-wafer bond can include transceivers for communicating data from the memory die 302 to the logic die via the wafer-on-wafer bond.

Figure 4:
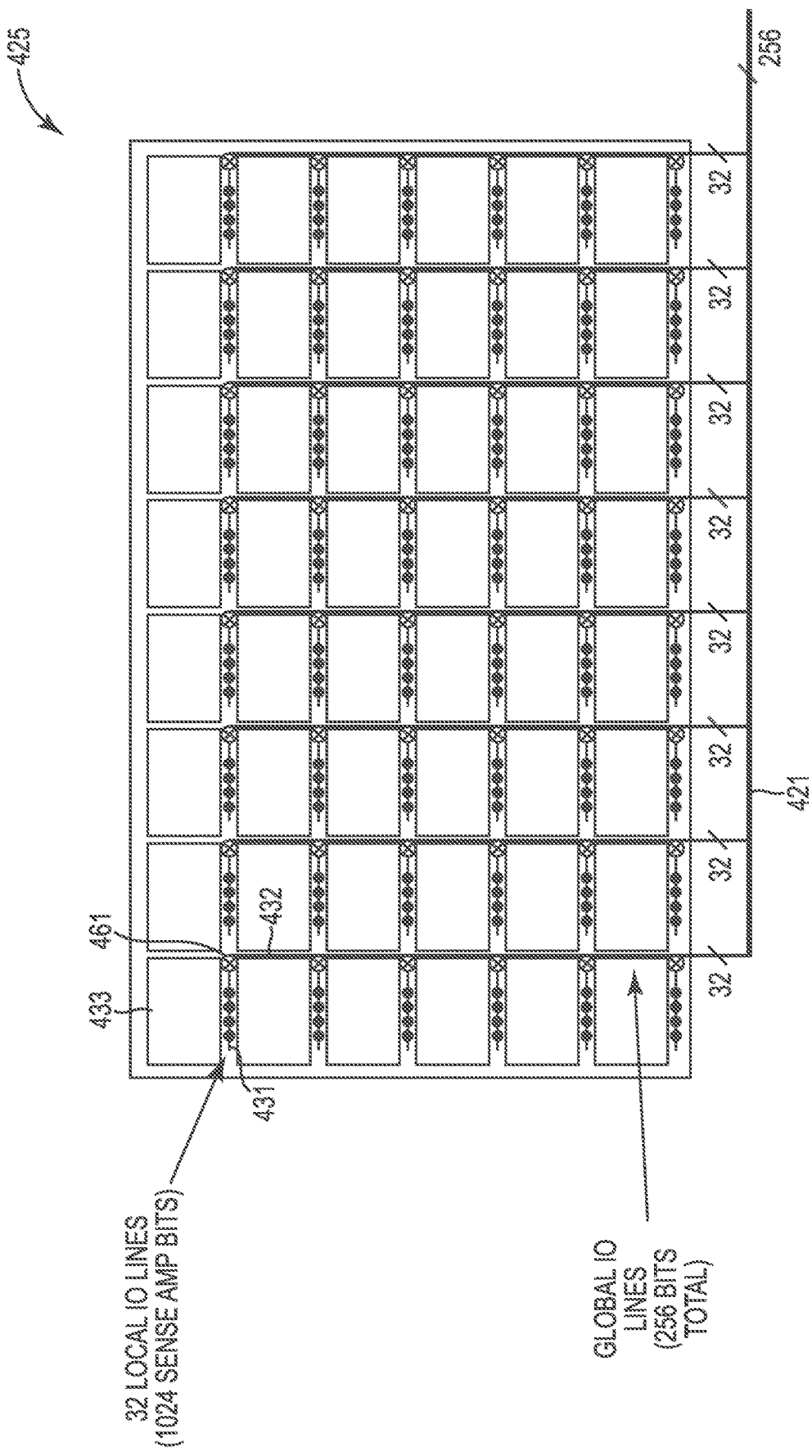
FIG. 4 illustrates a circuit diagram of a memory bank in accordance with a number of embodiments of the present disclosure.

FIG. 4 illustrates a memory bank 425 in accordance with a number of embodiments of the present disclosure. The memory bank 425 includes a quantity of memory tiles 433, each including a respective quantity of local IO lines 431 represented by the filled dots. Each tile 433 can include a quantity of rows and a quantity of columns of memory cells (e.g., 1024×1024). For example, each tile can include 32 LIOs 431. The LIOs 431 in each tile are coupled to a respective global TO line 432 and to a multiplexer 461, which may also be referred to in the art as a transceiver are referred to herein as multiplexers to differentiate from transceivers of the logic die configured to receive signals from the local IO lines 431, the global TO lines 432, and/or the global data bus 421.

The multiplexers 461 can be configured to receive signals from the local TO lines 431. The multiplexers 461 select a portion of the local TO lines 431. The multiplexers 461 can amplify the signals received from the selected portion of the local TO lines 431. The multiplexers 461 can also cause the amplified signals to be transmitted via the global IO lines 432. The multiplexers 461 can also receive signals from the global IO lines 432 and reduce the received signals. The multiplexers 461 can further transmit the reduced signals to the local IO lines 431.

The global IO lines 432 are coupled to the global data bus structure 421. Signals from multiple sense amplifiers can be multiplexed into the local IO lines 431. The local TO lines 431 can be coupled to the multiplexers 461 and transceivers (not shown) of the logic die via a wafer-on-wafer bond. The transceivers (not shown) of the logic die can cause signals from the local IO lines 431 to be provided to the logic die via the wafer-on-wafer bond. The wafer-on-wafer bond provides pitch control sufficiently fine to allow for contacts between the transceivers (not shown) and the local IO lines 431, which would otherwise not be possible.

In at least one embodiment, the transceiver (not shown) of the logic die can receive an enable/disable command from the corresponding logic die (e.g., as opposed to receiving the command from a host). In some embodiments, the enable/ disable command can be received by multiple transceivers of the logic die (e.g., the enable/disable command can cause signals indicative of data from a particular row in each bank 425 to be transferred via the corresponding transceivers). The control and operation of the multiple transceivers of the logic die is similar to having thousands of memory controllers, except that they transfer data rather than controlling all operations. Such operation can be beneficial, for example, for applications that involve massively parallel memory access operations. For an example memory device that is configured to include an 8 kilobit row, 256 bits of data can be prefetched per transceiver of the logic die. Therefore, each transceiver of the logic die can have 256 bits bonded out. In other words, at least one embodiment of the present disclosure can transfer 256 bits of data for each 8 kilobits of stored data (in this example architecture). In contrast, according to some previous approaches with an analogous architecture, a typical memory interface (e.g., via a global IO) would only be able to transfer 256 bits for 4 gigabits of stored data.

FIG. 5 illustrates a memory die 502 and a logic die 504 in accordance with a number of embodiments of the present disclosure. The memory die 502 can include a plurality of LIOs including a LIO 531. The logic die 504 can also include a plurality of LIOs including a LIO 541.

In various examples, signals can be routed from the memory die 502 to a LIO 541. Signals can also be routed from the LIO 541 to the memory die. The signals can be routed between the memory die 502 and the LIO 541 utilizing a transceiver of the memory die 502 and/or a transceiver of the logic die 504.

In a number of examples, signals can be routed from the memory die 502 to the logic die 504 utilizing a LIO 531 of the memory die 502. For example, signals can be routed from a memory array of the memory die 502 to the LIO 531 of the memory die 502. Signals can be routed from the LIO 531 to the LIO 541 of the logic die 504 utilizing a transceiver of the logic die. The signals can be routed to enable the logic die 504 to read data from the memory die 502. Signals can also be routed from the LIO 541 to the LIO 531 utilizing the transceiver of the logic die. The signals can be routed from the LIO 541 to the LIO 531 to allow the logic die 504 to write data to the memory die 502. The transceiver can be located in the logic die 504.

Figure 6A:
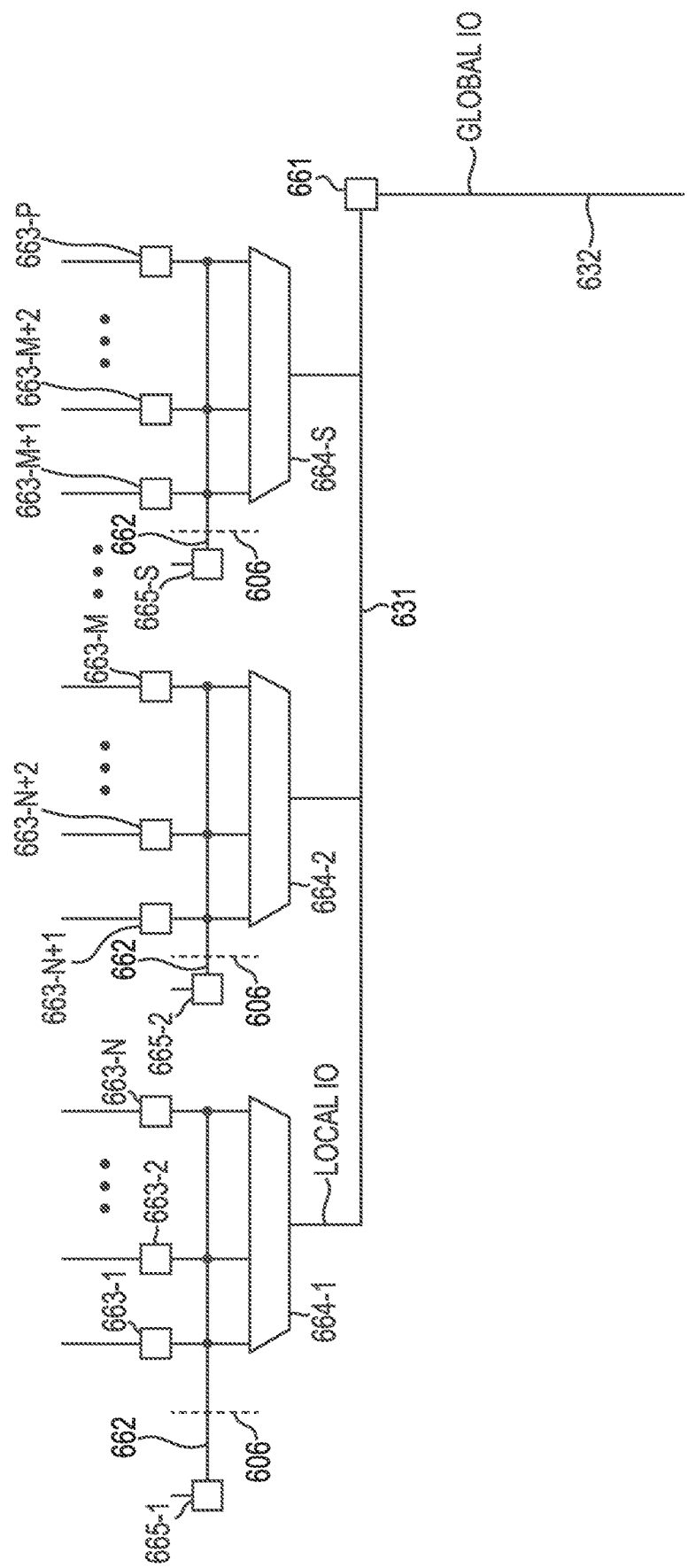
FIG. 6A illustrates a circuit diagram of sense amplifiers and multiplexers in accordance with a number of embodiments of the present disclosure.

FIG. 6A illustrates a circuit diagram of sense amplifiers 663-1, 663-2, . . . , 663-N, 663-N+1, 663-N+2, 663-M, 663-M+1, 663-M+2, 663-P and multiplexers 664-1, 664-2, . . . , 664-S in accordance with a number of embodiments of the present disclosure. The sense amplifiers 663-1, 663-2, . . . , 663-N, 663-N+1, 663-N+2, 663-M, 663-M+1, 663-M+2, 663-P can be referred to as sense amplifiers 663. The multiplexers 664-1, 664-2, . . . , 664-S can be referred to as multiplexers 664. FIG. 6A also includes the multiplexer 661 of the memory die.

The multiplexer 661 is differentiated from the transceivers 665-1, 665-2, . . . , 665-S. The multiplexer 661 can be configured to receive signals from the local IO lines 631. The multiplexer 661 selects a portion of the local IO lines 631. The multiplexer 661 can amplify the signals received from the selected portion of the local IO lines 631. The multiplexer 661 can also cause the amplified signals to be transmitted via the global IO lines 632. The multiplexer 661 can also receive signals from the global IO lines 632 and reduce the received signals. The multiplexer 661 can further transmit the reduced signals to the local IO lines 631. Although the multiplexer 661 is referred to as a multiplexer, the multiplexer 661 is different than the multiplexers 664 and has different functions than the multiplexers 664.

The transceivers 665-1, 665-2, . . . , 665-S can also receive signals, select a portion of the signals, amplify the portion of the signals, and transmit the amplified signals. However, the transceivers 665-1, 665-2, . . . , 665-S can transmit the amplified signals to the logic die and not the global IO lines 632.

FIG. 6A further includes transceivers 665-1, 665-2, . . . , 665-S of the logic die, referred to herein as transceivers 665. The memory die can include the sense amplifiers 663, the multiplexers 664, and the multiplexer 661. The memory die can also include an LIO 631 and a global IO (GIO) 632. For example, a memory tile 334, of FIG. 3, of the memory die can include the sense amplifiers 663, the multiplexers 664, the multiplexer 661, the LIO 631, and the GIO 632.

The memory tile can also include memory cells (not shown) that are programmable to store different states. Each of the memory cells may be programmable to store two states, denoted as a logic 0 and a logic 1. In some cases, a memory cell is configured to store more than two logic states. A memory cell may include a capacitor to store a charge representative of the programmable states; for example, a charged and uncharged capacitor may represent two logic states. DRAM architectures may commonly use such a design, and the capacitor employed may include a dielectric material with linear electric polarization properties.

Operations such as reading and writing may be performed on memory cells by activating or selecting the appropriate access line and sense line. Activating or selecting an access line or a sense line may include applying a voltage potential to the respective line. As used herein, activating or selecting an access line can be referred to as activating or selecting a row of memory cells. Access lines and sense lines may be made of conductive materials. In some examples, access lines and sense lines are made of metals (e.g., copper, aluminum, gold, tungsten, etc.). Each row of memory cells is connected to a single access line, and each column of memory cells are connected to a single sense line. By activating one access line and one sense line, a single memory cell may be accessed at their intersection. The intersection of an access line and a sense line may be referred to as an address of a memory cell. By activating one access line and a plurality of sense lines, a row of memory cells may be access. The intersection of the plurality of access lines and the sense line may be referred to as an address of a row of memory cells.

In some architectures, the storage component of a cell (e.g., a capacitor) may be electrically isolated from the digit line by a selection device. The access line may be connected to and may control the selection device. For example, the selection device may be a transistor and the access line may be connected to the gate of the transistor. Activating the access line results in an electrical connection between the capacitor of a memory cell and its corresponding sense line. The sense line may then be accessed to either read or write the memory cell.

Accessing memory cells may be controlled through a row decoder and a column decoder (not shown). For example, a row decoder may receive a row address from the memory controller (e.g., control circuitry) and activate the appropriate access line based on the received row address. Similarly, a column decoder receives a column address from the memory controller and activates the appropriate sense line. Thus, by activating an access line and a sense line, a memory cell may be accessed. By activating an access line and a plurality of sense lines, a row or memory cells may be accessed.

Upon accessing, a memory cell may be read, or sensed, by sensing circuitry. The sensing circuitry can comprise the sense amplifiers 663. For example, sense amplifiers 663 may compare a signal (e.g., a voltage) of the relevant sense line to a reference signal (not shown) in order to determine the stored state of the memory cells. If a sense line has a higher voltage than the reference voltage, then sense amplifiers 663 may determine that the stored state in a corresponding memory cell was a logic 1 and vice versa. The sense amplifiers 663 may include various transistors or amplifiers in order to detect and amplify a difference in the signals, which may be referred to as latching. The sense amplifiers 663 can represent a stripe of multiple sense amplifiers. The detected logic state of memory cell may then be output through column decoder and to an LIO 631. In various instances the sense amplifiers 663-1, 663-2, . . . , 663-N can be a first stripe of sense amplifiers. The sense amplifiers 663-N+1, 663-N+2, 663-M can be a second stripe of sense amplifiers. The sense amplifiers 663-M+1, 663-M+2, 663-P can be a third stipe of sense amplifiers.

In various examples, the wafer-on-wafer bond 606 can couple the output of the sense amplifiers 663 to the transceivers 665 of the logic die. The transceivers 665 can be controlled by the logic die to cause the output of the sense amplifiers 663 to be provided to circuitry of the logic die. For examples, a transceiver 665-1 can cause signals outputted from the sense amplifiers 663-1, 663-2, . . . , 663-N to be provided to circuitry of the logic die that is downstream from the transceiver 665-1. Although a single transceiver 665-1 is shown, the transceiver 665-1 can represent multiple transceivers such that each of the outputs of the sense amplifiers 663-1, 663-2, . . . , 663-N is provided concurrently to the circuitry downstream from the multiple transceivers of the logic die. The transceivers 665-2 can cause the output of the sense amplifiers 663-N-1, 663-N+2, 663-M to be provided to circuitry of the logic die. The transceivers 665-S can cause the output of the sense amplifiers 663-M+1, 663-M+2, 663-P to be provided to circuitry of the logic die.

A memory controller (e.g., the control circuitry of the logic die) can send a signal to the transceivers 665, to selectively route the signals representing data off-chip (e.g., to a logic die "to DLA"). The illustrated path from the sense amplifiers 663 to the transceivers 665 of the logic die is a representation of the electrical pathway between a memory tile and the corresponding logic die. Embodiments of the present disclosure can preserve the functionality and fabrication of a standardized memory interface while allowing for the functionality and fabrication of an additional high bandwidth interface from the memory die to a logic die via the wafer-on-wafer bond 606.

In various examples, each of the transceivers 665 can be coupled to a plurality of sense amplifiers 663. For example, the transceiver 665-1 can be coupled to the sense amplifiers 663-1, 663-2, . . . , 663-N. The transceiver 665-2 can be coupled to the sense amplifiers 663-N+1, 663-N+2, 663-M. The transceiver 665-S can be coupled to the sense amplifiers 663-M+1, 663-M+2, 663-P. In various instances, each of the transceivers 665 can direct a plurality of signals. For example, the transceiver 665-1 can direct the signals provided from the sense amplifiers 663-1, 663-2, . . . , 663-N at a same time. The transceiver 665-2 can redirect the signals provided from the sense amplifiers 663-N+1, 663-N+2, 663-M at a same time. The transceiver 665-S can direct signals provided from the sense amplifiers 663-M+1, 663-M+2, 663-P at a same time.

A memory cell may be set, or written, by activating the relevant access line and sense line. Activating an access line electrically connects the corresponding row of memory cells to their respective digit lines. By controlling the relevant sense line while the access line is activated, a memory cell may be written (a logic value may be stored in the memory cell). A column decoder may accept data, for example, via the LIO 631, to be written to the memory cells. A column decoder may also accept data from the transceivers 665 to be written to the memory cells. For example, the column decoder may configure memory cells to store signals while a memory controller of the logic die configures the transceivers 665 to route data to the sense amplifiers 663. In various examples, the lines coupling the transceivers 665 to the wafer-to-wafer bond 606 can be referred to as LIOs 662 of the logic die. The lines 662 that couple the transceivers 665 to downstream circuitry of the logic die can also be referred to as LIOs 662 of the logic die.

A memory controller of the logic die can cause signals representing data to be received at the logic die from atypical I/O path including the LIOs 631 utilizing the transceiver 665. The memory controller of the memory die can also cause signals representing data to be provided through a typical input/output path utilizing the LIOs 631, the multiplexer 661, and the global IO 632.

In some memory architectures, accessing the memory cell may degrade or destroy the stored logic state and re-write or refresh operations may be performed to return the original logic state to memory cell. In DRAM, for example, the capacitor may be partially or completely discharged during a sense operation, corrupting the stored logic state. Additionally, activating a single access line may result in the discharge of all memory cells in the row; thus, several or all memory cells in the row may need to be re-written. Some memory architectures, including DRAM, may lose their stored state over time unless they are periodically refreshed by an external power source. For example, a charged capacitor may become discharged over time through leakage currents, resulting in the loss of the stored information. Logic states may be re-written during a re-write operation or refreshed during a refresh operation.

The memory controller may control the operation (e.g., read, write, re-write, refresh, etc.) of memory cells through the various components, for example, a row decoder, a column decoder, and/or sense amplifiers 663. The memory controller may generate row and column address signals in order to activate the desired access lines and sense lines. The memory controller may also generate and control various voltage potentials used during the operation of memory tiles. For example, memory controller may operate a selection component to isolate a sense line (e.g., from a corresponding capacitor) during sensing. In general, the amplitude, shape, or duration of an applied voltage discussed herein may be adjusted or varied and may be different for the various operations for operating memory array. Furthermore, one, multiple, or all memory cells within the memory tile may be accessed simultaneously; for example, multiple or all cells of memory tile may be accessed simultaneously during a reset operation in which all memory cells, or a group of memory cells, are set to a single logic state.

In various instances, the transceivers 665 can route signals concurrently. For example, the transceiver 665-1 can route signals between the sense amplifiers 663-1, 663-2, . . . , 663-N and the logic die concurrently with the routing of signals by the transceiver 665-2, . . . , and/or transceiver 665-S. In various examples, the transceiver 665-1 can route signals between the sense amplifiers 663-1, 663-2, . . . , 663-N and the logic die concurrently.

Although not shown, the transceivers of the logic die coupled to a plurality of tiles can route signals from the memory die to the logic die concurrently. For example, the transceivers 665 can route data with other transceivers coupled to different tiles concurrently. A controller can activate rows of a plurality of tiles concurrently to cause corresponding sense amplifiers (e.g., including sense amplifiers 663) to latch signals. The transceivers (e.g., including the transceivers 665) coupled to different tiles can route signals from the sense amplifiers of a plurality of tiles to a logic die concurrently. The logic die can concurrently receive a greater quantity of signals from the memory die via the transceivers 665 than would be possible to output via the GIOs 632 or a GBUS. Likewise, the logic die can provide a greater quantity of signals concurrently to the memory die via the transceivers 665 than would be possible via the GIO 632 or GBUS. Transceivers 665 can also route signals concurrently with the routing of data by transceivers coupled to different banks via the wafer-on-wafer bond 606.

In various examples, the memory die can output data to the GIOs 632 and the transceivers 665 concurrently. For example, a memory controller of a memory device can activate the LIOs 631 and the GIOs 632 concurrently with the activation of the transceivers 665, by a memory controller of the logic die, to output signals to the logic die and to output signals through the traditional IO circuitry comprising the GIO 632.

In various instances, signals can be provided from a GBUS (e.g., GBUS 321 in FIG. 3) of the memory die to a logic die. A transceiver of the logic die, coupled to the GBUS, can be configured to route data from the memory die to the logic die. For example, the transceiver of the logic die can be activated to route signals from the GBUS to the logic die. The transceivers configured to route signals from the GBUS to the logic die can be different than the transceivers configured to route signals from the LIO 631 to the logic die. Two independent paths can be provided for routing signals from the memory die to the logic die. The first path can originate at the LIO 631 while the second path can originate at a GBUS of the memory die. The first path can be utilized by activating a number of transceivers of the logic die while a second path can be utilized by activating a different number of transceivers of the logic die. In various instances, the quantity of signals that can be routed concurrently from the LIO 631 to the logic die can be greater than the quantity of signals that can be routed concurrently from the GBUS to the logic die.

Figure 6B:
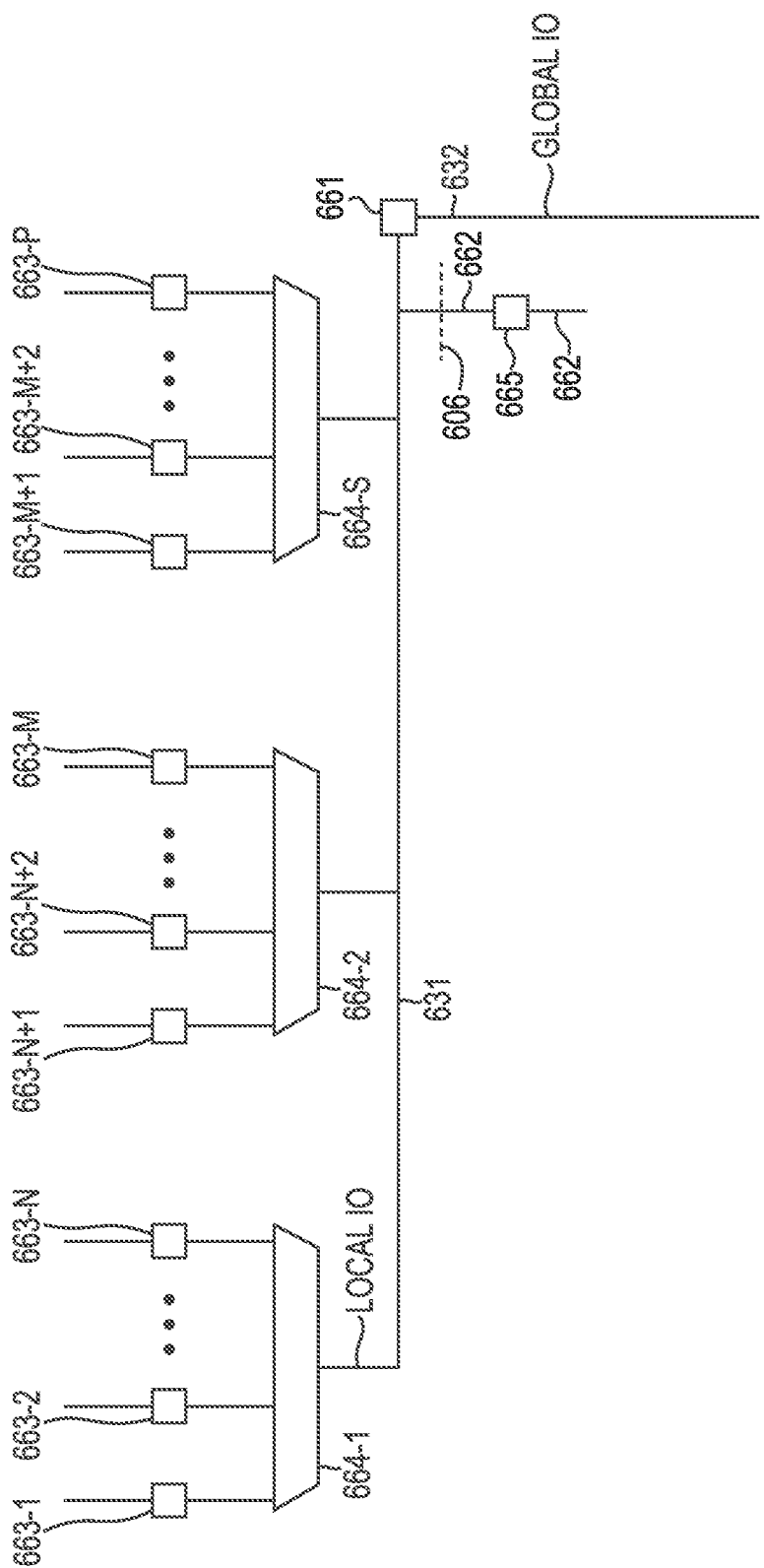
FIG. 6B illustrates a circuit diagram of a local input output (LIO) line in accordance with a number of embodiments of the present disclosure.

FIG. 6B illustrates a circuit diagram of a LIO 631 in accordance with a number of embodiments of the present disclosure. In FIG. 6B the transceiver 665 is coupled to the LIO 631 as compared to FIG. 6A where the transceivers 665 are coupled to the sense amplifiers 663.

In FIG. 6B, the sense amplifiers 663 can output a plurality of signals. The signals can be output to the multiplexers 664. For example, the sense amplifiers 663-1, 663-2, ..., 663-N can output a first plurality of signals to the multiplexer 664-1. The sense amplifiers 663-N+1, 663-N+2, 663-M can output a second plurality of signals to the multiplexer 664-2 while the sense amplifiers 663-M+1, 663-M+2, 663-P can output an Sth plurality of signals to the multiplexer 664-S. As used herein, "Sth" represents a variable such that "Sth plurality of signals" represents a variable plurality of signals.

Each of the multiplexers 664 can output a plurality of signals to the LIOs 631. For example, the multiplexer 664-1 can output a first portion of the first plurality of signals, the multiplexer 664-2 can output a second portion of the second plurality of signals, ..., the multiplexer 664-S can output an Sth portion of the Sth plurality of signals.

The transceiver 665 can route the signals of the LIOs 631 of the memory die to an LIO 662 of the logic die, for example. In various examples, the memory device can activate the multiplexer 661 to output signals from the LIOs 631 to the GIOs 632 through a traditional IO circuitry of the memory device. The logic die can concurrently activate the transceiver 665 with the activation of the LIOs 631 and the GIOs 632 to output data to the logic die with the concurrent outputting of the data via the IO circuitry of the memory die. For example, a memory controller of the memory device can be used to determine whether to output data through the traditional IO circuitry of the memory device while a memory controller of the logic die is used to determine whether to output data to the logic die bonded to the memory die.

Although a single transceiver 665 is shown, a plurality of transceivers can be utilized to route signals from a plurality of LIOs of a memory die to the logic die. For example, a first transceiver can be coupled to a first LIO of a first tile of the memory die. A second transceiver can be coupled to a second LIO of a second tile of the memory die, etc. Each of the transceivers can route signals to the logic die by routing the signals to LIOs 662 of the logic die. Each of the transceivers can route signals concurrently.

In various instances, the transceiver 665 can be coupled to the GIO 632 instead of the sense amplifiers 663 or the LIO 631. Similarly, the transceivers coupled to the GIOs can concurrently route signals to the logic die.

To concurrently route signals from the memory die to the logic die, the memory controller can activate a plurality of rows of a plurality of tiles. For example, a row for each of the tiles of a memory die can be activated concurrently to route data from the memory die to the logic die. In various examples, routing signals to the logic die via transceivers of the logic die can include routing signals to a processing resource of the logic die. For example, data can be routed to a DLA of the logic die or a different processing resource of the logic die.

Figure 7:
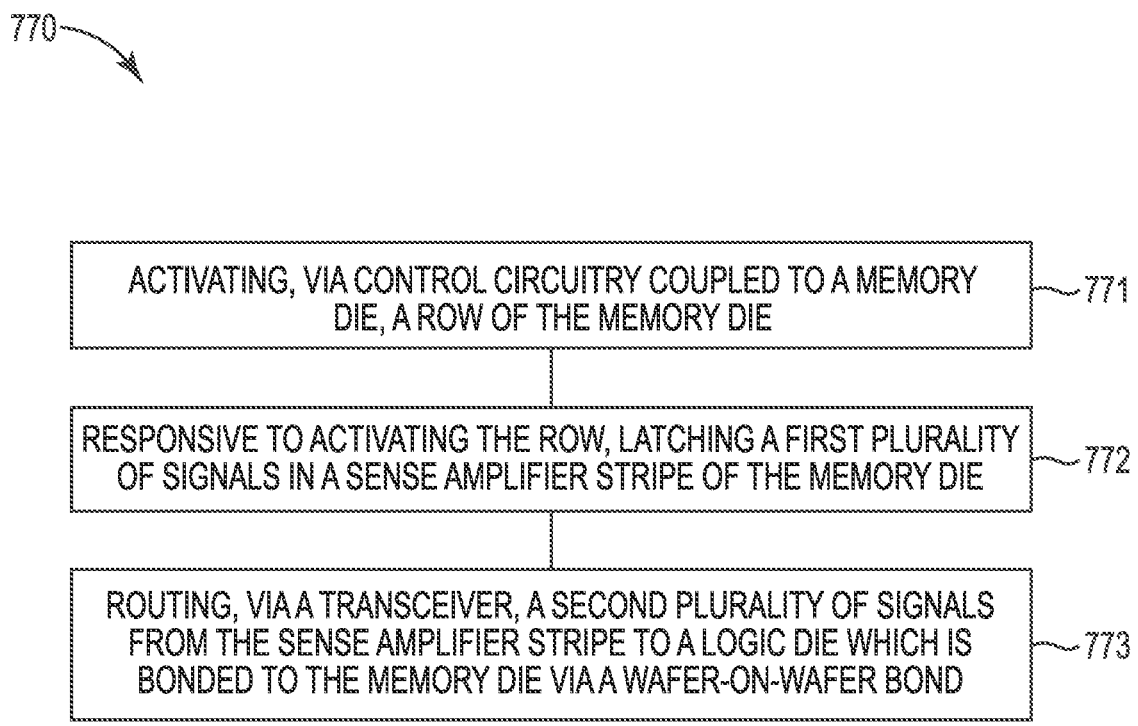
FIG. 7 is a flow diagram corresponding to a method for routing signals between a memory die to a logic die in accordance with some embodiments of the present disclosure.

FIG. 7 is a flow diagram corresponding to a method 770 for routing signals between a memory die to a logic die in accordance with some embodiments of the present disclosure. At operation 771, a row of the memory die can be activated via control circuitry coupled to the memory die. The memory die can be bonded to a logic die via a wafer-on-wafer bond.

At operation 772, responsive to activating the row, a first plurality of signals can be latched in a sense amplifier stripe of the memory die. The sense amplifier stripe can be comprised of a plurality of sense amplifiers. The sense amplifier stripe can be incorporated in a tile of the memory die.

At operation 773, a second plurality of signals can be routed using a transceiver from the sense amplifier stripe to a logic die. The second plurality of signals can be generated from the first plurality of signals by the sense amplifiers. The second plurality of signals can be routed to the logic die concurrently.

A control circuitry can configure a plurality of multiplexers to route the second plurality of signals from the sense amplifier stripe to a global data bus of the memory die. The second plurality of signals can be routed from the sense amplifier stripe to the global data bus to output the second plurality of signals via IO circuitry of the memory device comprising the memory die. The transceivers can be configured by control circuitry of the logic die to route the second plurality of signals to the logic die concurrently with a routing of the second plurality of signals to the global data bus. That is, a memory die can output the second plurality of signals to the logic die and to the IO circuitry of the memory device.

A third plurality of signals can be received from the logic die at the sense amplifier stripe to store the third plurality of signals in the memory die. For example, a processing resource of the logic die can perform a plurality of operation on data received from the memory die. The output of the plurality of operations can comprise signals that can be routed from the logic die to the sense amplifier stripe to store the third plurality of signals in the memory die. In this respect, the memory die can be used as SRAM for the memory die. In various instances, the memory die can be used to output data from the logic die. The logic die may not have a direct connection to a plurality of pins of the memory device without going through the memory die to which the logic die is bonded. The logic die can route signals representing data to the memory die. The memory die can then output the signals to the IO circuitry of the memory device to output data from the logic die to the pins of the memory device.

Responsive to the transceiver routing the second plurality of signals, a global data bus of the memory die may not be activated. Refraining from activating the global data bus can prevent the signals from being output from the memory die to the IO circuitry of the memory device.

The second plurality of signals can be routed to a processing resource of the logic die. The second plurality of signals can be routed to the processing resource to allow the processing resource to perform a plurality of operations. Using the second plurality of signals.

In various instances, a plurality of rows of memory cells of a memory die can be activated. The plurality of rows can be activated concurrently. Responsive to activating the plurality of rows of memory cells, a first plurality of signals can be latched in a plurality of sense amplifiers. The plurality of sense amplifiers can correspond to the plurality of rows. For example, a first row can correspond to a first plurality of sense amplifiers. A second row can correspond to a second plurality of sense amplifiers, and so forth. Each of the plurality of rows can correspond to a different tile of a memory die.

A second plurality of signals provided by the plurality of sense amplifiers can be multiplexed onto a plurality of LIO lines. The plurality of LIO lines can comprise the LIO. A multiplexed signal can be routed, via a respective transceiver coupled to each of the plurality of LIO lines, from the corresponding LIO line to a logic die bonded to the memory die. A multiplexed signal can be a signal that has been multiplexed by a multiplexer onto the plurality of lines. In various instances, a different transceiver can be coupled to each of the LIO lines or a transceiver can be configured to route a plurality of signals concurrently from the LIO lines to the logic die.

Each of the plurality of rows can correspond to a different tile from a plurality of tiles of the memory die. The plurality of rows which are similarly located in each of a plurality of tiles of the memory die can be activated. Activating the plurality of rows can include activating a first row in a first location of the first tile, a second row in a first location of the second tile, a third row in a first location of the third tile, etc.

The second plurality of signals can be multiplexed on a sense amplifier stripe base. For example, a first sense amplifier stripe can be multiplexed using a first multiplexer while a second sense amplifier stripe can be multiplexed using a second multiplexer, etc.

A third plurality of signals can be routed, via the respective transceiver coupled to each of the plurality of LIO lines, from the logic die to the corresponding LIO line. Signals can be routed from the logic die to the LIO lines of a memory die to store data in the memory die.

In various instances, signals can be routed from a LIO line of the memory die to a LIO line of the logic die. For example, multiplexed signals can be routed from a corresponding LIO line of the memory die to a different LIO line of the logic die.

In various examples, a memory device can comprise a memory die, a logic die, and a plurality of transceivers. The memory die can comprise a plurality of sense amplifiers stripes and control circuitry. The logic die can be conde dot the memory die.

The control circuitry can active a plurality of rows of the memory die. Responsive to activating the plurality of rows, the control circuitry can latch a plurality of signals in the sense amplifier stripes. The plurality of transceivers can route a second plurality of signals from the plurality of sense amplifier stripes to the logic die. That is, the transceivers can route signals directly from the sense amplifiers of the sense amplifiers stripes to the logic die. The plurality of transceivers can be configured to receive control signals to route the data corresponding to the first plurality of signals from the plurality of sense amplifier stripes to the logic die. The control signals can be received from the logic die even though the transceivers are located on the memory die. For example, the plurality of transceivers can be configured to receive the control signals from a DLA of the logic die. The plurality of transceivers can be configured to, responsive to receipt of the control signals, route the data concurrently. For example, the logic die can control the flow of signals from the memory die to the logic die by controlling the transceiver. Each transceiver from the plurality of transceivers can further be configured to, responsive to receipt of the control signals, route a different portion of the data concurrently with the routing of other portions of the data. For example, a first transceiver and a second transceiver can receive control signals from the logic die concurrently. The first transceiver and the second transceiver can route signals concurrently to the logic die. For example, the first transceiver can be route a first plurality of signals concurrently with the routing of a second plurality of signals by the second transceiver.

As used herein, "a number of" something can refer to one or more of such things. For example, a number of memory devices can refer to one or more memory devices. A "plurality" of something intends two or more.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure. It is to be understood that the above description has been made in an illustrative fashion, and not a restrictive one. Combinations of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:
activating, via control circuitry coupled to a memory die, a row of the memory die;
responsive to activating the row, latching a first plurality of signals in a sense amplifier stripe of the memory die;
routing, via a transceiver, a second plurality of signals from the sense amplifier stripe to a logic die which is bonded to the memory die via a wafer-on-wafer bond; and
receiving a third plurality of signals from the logic die at the sense amplifier stripe to store the third plurality of signals in the memory die.

2. The method of claim 1, further comprising configuring, via the control circuitry, a plurality of multiplexers to route the second plurality of signals from the sense amplifier stripe to a global data bus of the memory die.

3. The method of claim 2, further comprising configuring the transceiver to route the second plurality of signals to the logic die concurrently with a routing of the second plurality of signals to the global data bus.

4. The method of claim 1, further comprising, responsive to the transceiver routing the second plurality of signals, refraining from activating a global data bus of the memory die.

5. The method of claim 1, further comprising, routing the second plurality of signals to a processing resource of the logic die.

6. A method, comprising:
activating a plurality of rows of memory cells of a memory die;
responsive to activating the plurality of rows of memory cells, latching a first plurality of signals in a plurality of sense amplifiers;
multiplexing a second plurality of signals provided by the plurality of sense amplifiers onto a plurality of local input/output (LIO) lines; and
routing, via a respective transceiver coupled to each of the plurality of LIO lines, a multiplexed signal, of the second plurality of multiplexed signals, from a corresponding LIO line to a logic die bonded to the memory die via a wafer-on-wafer bond.

7. The method of claim 6, further comprising activating the plurality of rows each of which corresponds to a different tile from a plurality of tiles of the memory die.

8. The method of claim 6, further comprising activating the plurality of rows which are similarly located in each of a plurality of tiles of the memory die.

9. The method of claim 6, further comprising latching the first plurality of signals in sense amplifier stripes comprising the plurality of sense amplifiers.

10. The method of claim 9, further comprising multiplexing the second plurality of signals on a sense amplifier stripe basis.

11. The method of claim 9, further comprising receiving, via the respective transceiver coupled to each of the plurality of LIO lines, a third plurality of signals from the logic die to the corresponding LIO line.

12. The method of claim 6, further comprising activating the plurality of rows concurrently.

13. The method of claim 6, further comprising routing the multiplexed signal from the corresponding LIO line of the memory die to different LIO line of the logic die.

14. An apparatus, comprising:
a memory die;
a logic die bonded to the memory die via a wafer-on-wafer bond;
a plurality of transceivers coupled to a plurality of sense amplifier stripes of the memory die; and
control circuitry coupled to the memory die and configured to:
activate a plurality of rows of the memory die; and
responsive to activating the plurality of rows, latch a first plurality of signals in the sense amplifier stripes;
wherein the plurality of transceivers are configured to;
receive control signals from a deep learning accelerator (DLA) of the logic die to route data corresponding to the first plurality of signals from the plurality of sense amplifier stripes to the logic die;
route a second plurality of signals from the plurality of sense amplifier stripes to the logic die.

15. The apparatus of claim 14, wherein the plurality of transceivers are configured to, responsive to receipt of the control signals, route the data concurrently.

16. The apparatus of claim 14, wherein each transceiver from the plurality of transceivers is configured, responsive to receipt of the control signals, to route a different portion of the data concurrently with a routing of other portions of the data.

17. A method, comprising:
activating, via control circuitry coupled to a memory die, a row of the memory die;
responsive to activating the row, latching a first plurality of signals in a sense amplifier stripe of the memory die;
routing, via a transceiver, a second plurality of signals from the sense amplifier stripe to a logic die which is bonded to the memory die via a wafer-on-wafer bond; and
responsive to the transceiver routing the second plurality of signals, refraining from activating a global data bus of the memory die.

* * * * *